US00PP10369P

United States Patent [19]

Bak et al.

[11] Patent Number: Plant 10,369

[45] Date of Patent: Apr. 28, 1998

[54] GUZMANIA PLANT NAMED 'SALSA'

[75] Inventors: Gerardus J. Bak, Assendelft; Nicolaas D. Steur, Oude Niedorp; Elly Bak, Rijsenhout, all of Netherlands

[73] Assignee: Corn. Bak B.V., Assendelft, Netherlands

[21] Appl. No.: 717,914

[22] Filed: Sep. 23, 1996

[51] Int. Cl.[6] ..... A01H 5/00

[52] U.S. Cl. ..... Plt./88.8

[58] Field of Search ..... Plt./88.8

[56] References Cited

U.S. PATENT DOCUMENTS

P.P. 8,514 12/1993 Bak et al. ..... Plt./88.8

*Primary Examiner*—James R. Feyrer

*Assistant Examiner*—Kent L. Bell

*Attorney, Agent, or Firm*—Foley & Lardner

[57] ABSTRACT

A new cultivar of Guzmania named 'Salsa' characterized by its red-purple or lilac scape bracts and its bright white top primary bracts, with the bracts just below the top primary bracts being white infused with lilac primarily at the base and tip, white flowers on many branches, relatively large growth habit, superior floral bract production, and its long lasting habit.

2 Drawing Sheets

The present invention relates to a new and distinct cultivar of Guzmania that is an interspecific hybrid, hereinafter referred to by the cultivar name 'Salsa'.

Guzmania are predominantly epiphytic with a few terrestrial species and are native to the tropics. For the most part species vary in diameter from 7 or 8 inches to 3 or 4 feet and have rosettes of glossy, smooth edged leaves.

Floral bracts of Guzmania frequently have brilliant colors and may last for many months. The range of bract color for Guzmania is generally from yellow through orange but may also include flame red and red-purple. White or yellow, tubular, three petalled flowers may also appear on a stem or within the leaf rosette but are usually short lived.

Guzmania may be advantageously grown as pot plants for greenhouse or home use. Desirably the plants are shaded from direct sunlight and during the spring to autumn period the central vase-like part of the leaf rosette is desirably filled with water.

Guzmania is native to tropical America. Leaves of Guzmania are usually formed as basal rosettes which are stiff and entire and in several vertical ranks. Guzmania have terminal spikes or panicles which are often bracted with petals united in a tube about as long as the calyx. The ovary is superior and the seeds plumose.

Asexual propagation of Guzmania is frequently done through the use of tissue culture practices. Propagation can also be from off-shoots produced by the plant which may then be rooted. The resulting plantlets are detached from the mother plant and may be potted up in a suitable growing mixture.

The new cultivar 'Salsa' is a product of a planned breeding program and was originated by the inventors from a cross made during such program in Assendelft, The Netherlands, in 1986. The male or pollen parent was a selection of *Guzmania wittmackii* identified by Code No. 8626202. The female or seed parent was a selection of *Guzmania lingulata minor* identified by Code No. 8626204. Both parents have a degree of homozygosity such that the progeny of the cross were and continue to be surprisingly uniform.

The selection comprising the new variety was chosen after commencement of flowering of the progeny in 1988 in Assendelft, The Netherlands. The selection was first asexually propagated through off-shoots by or under the supervision of the inventors in Assendelft, with subsequent asexual reproduction being primarily by tissue culture. Continuous asexual propagation has demonstrated that the combination of characteristics as herein disclosed for the new cultivar 'Salsa' are firmly fixed and are retained through successive generations of asexual reproduction.

'Salsa' is particularly characterized by the following:

1. Relative large growth habit in a funnel form rosette, measuring approximately 45 cm in height above the pot when flowering, and 65 cm. in diameter.
2. Superior floral bract production.
3. Scape bracts are red-purple or lilac with dark green tips. The top primary bracts are essentially all white (158C) with occasional slight infusion and tipping of red-purple. The bracts between the scape bracts and the essentially all white top primary bracts are also white in base color, but are infused more heavily with red-purple, particularly in the base and tip regions. The lilac and white bract color is beautifully striking.
4. The flowers are white, being approximately 80 in number divided over approximately 12 branches within the floral bracts.
5. 'Salsa' is an excellent growing, long lasting plant.

The closest comparison cultivar is Guzmania 'Limbo.' The bracts of 'Limbo' are predominantly lilac, but the lilac color is slightly different than the color of 'Salsa.' The white primary bract color of 'Salsa' is much more bright and more extensive, thereby giving 'Salsa' a more lilac-white inflorescence.

'Salsa' has not been tested under all available environmental conditions. The phenotype may vary with variations in environmental conditions such as temperature, light intensity, day length and humidity without, however, any change in the genotype of the new cultivar.

In the accompanying color photographic drawings, the photo on sheet 1 is a top perspective view of 'Salsa.' The photo on sheet 2 comprises a close-up view showing in more detail the flowers, the floral bracts and the primary bracts. The colors are as true as possible with illustrations of this type.

In the following description, color references are made to The Royal Horticultural Society Colour chart (R.H.S.).

The following traits have been repeatedly observed and in combination distinguish 'Salsa' as a new and distinct cultivar. These observations, measurements and descriptions are based on greenhouse conditions in Assendelft, The Netherlands.

I. Plant:

*Form.*—Funnel form rosette.

*Height.*—Approximately 45 cm high when flowering.

*Growth habit.*—Stemless.

*Diameter.*—Approximately 65 cm.

II. Foliage:

*Size of leaf.*—Length: Approximately 30–42 cm long. Width: Approximately 3–4 cm.

*Shape of leaf.*—Linear — lanceolate.

*Surface texture.*—Smooth.

*Variegation.*—None.

*Color.*—Upperside, 147A. Underside, 147A. The color of the leaves can vary somewhat depending on environmental conditions including the amount of fertilizer used.

III. Bracts:

*Length.*—The lowest scape bracts are approximately 28 cm long. The bracts just below the primary bracts are approximately 10 cm long. The lowest primary bracts are approximately 10 cm long, becoming shorter to approximately 4 cm in length at the top.

*Width.*—The scape bracts are approximately 3.5 cm wide, and the primary bracts are approximately 3.0 cm wide.

*Number.*—There are approximately 11 scape bracts and 14 primary bracts joining the primary bracts in making a full inflorescence.

*General shape.*—Lanceolate.

*Texture.*—Smooth.

*Margin.*—Entire.

*Color.*—The upper surface of the scape bracts is 60A–60B, with the scape bract tips being 147A; the upper surface of the primary bracts is 60A–60C, with the top primary bracts being white 147A; the bracts just below the top primary bracts are 158C infused with 60A–C at the base and tip; the top primary bracts are 158C; occasionally slightly infused with 60A–60C at the base and tip.

IV. Flowers:

*Borne (stalks).*—Erect

*Shape of inflorescence.*—Compound

*Size of inflorescence on stalk.*—The size of the inflorescence changes with maturity; at full flowering, Inflorescence is approximately 14 cm in height and approximately 24 cm in diameter.

*Individual petals* (Disposed within the floral bracts hidden behind the primary bracts).—1) Length: Approximately 5.0 cm. 2) Width: Approximately 0.5 cm. 3) Quantity: Approximately 80 flowers divided over approximately 12 branches depending on the size of the plant. 4) Color: White.

*Time of blooming.*—A fully grown plant can bloom the entire year. Flowering starts approximately 15 weeks after natural induction or through treatment with acetylene.

*Duration of blooms.*—Each flower blooms one day and the total blooming period is about 5 weeks.

V. Reproductive organs:

*Ovaries.*—Superior.

*Stamen.*—6 in number.

VI. Seed characteristics: Sterile hybrid, therefore no fruit or seed.

I claim:

1. A new and distinct cultivar of Guzmania plant named 'Salsa', as illustrated and described.

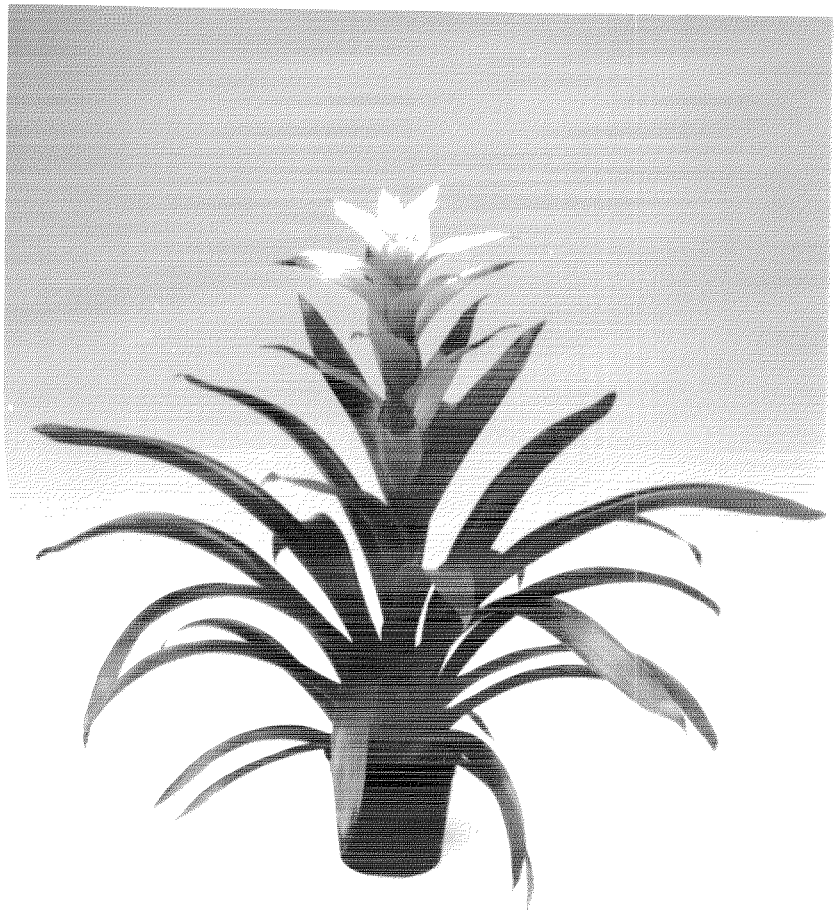

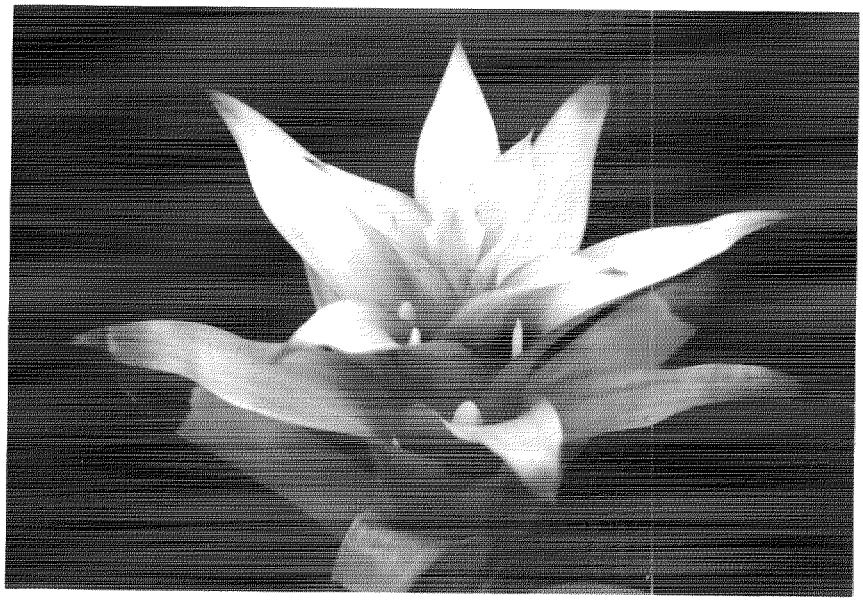

* * * * *